(12) United States Patent
Xu et al.

(10) Patent No.: US 10,392,598 B2
(45) Date of Patent: Aug. 27, 2019

(54) METHODS OF MEASURING CELL PURITY FOR MAKING QUALITY CONTROL DETERMINATIONS AND RELATED COMPOSITIONS

(71) Applicants: Emory University, Atlanta, GA (US); Children's Healthcare of Atlanta, Inc., Atlanta, GA (US)

(72) Inventors: Chunhui Xu, Decatur, GA (US); Shuming Nie, Atlanta, GA (US); Jingjia Han, Atlanta, GA (US)

(73) Assignees: Emory University, Atlanta, GA (US); Children's Healthcare of Atlanta, Inc., Atlanta, GA (US)

( * ) Notice: Subject to any disclaimer, the term of this patent is extended or adjusted under 35 U.S.C. 154(b) by 0 days.

(21) Appl. No.: 15/738,109

(22) PCT Filed: Jun. 17, 2016

(86) PCT No.: PCT/US2016/038121
§ 371 (c)(1),
(2) Date: Dec. 19, 2017

(87) PCT Pub. No.: WO2016/205678
PCT Pub. Date: Dec. 22, 2016

(65) Prior Publication Data
US 2018/0171287 A1   Jun. 21, 2018

Related U.S. Application Data

(60) Provisional application No. 62/182,012, filed on Jun. 19, 2015.

(51) Int. Cl.
*G01J 3/44* (2006.01)
*C12N 5/00* (2006.01)
(Continued)

(52) U.S. Cl.
CPC ......... *C12N 5/0081* (2013.01); *C08G 65/334* (2013.01); *G01J 3/44* (2013.01);
(Continued)

(58) Field of Classification Search
CPC ........ G01N 21/64; G01N 21/65; G01N 33/56; G01N 33/58; G01J 3/02; G01J 3/44; C12N 5/00; C08G 65/334
See application file for complete search history.

(56) References Cited

U.S. PATENT DOCUMENTS 7,588,827 B2  9/2009  Nie
8,170,665 B2  5/2012  Cohen
(Continued)

FOREIGN PATENT DOCUMENTS

| CN | 104387790 A | 11/2014 |
|---|---|---|
| WO | 2009099552 | 8/2009 |
| WO | 2015123005 | 8/2015 |

OTHER PUBLICATIONS

Han et al. Novel Surface-Enhanced Raman Scattering-based Assays for Ultra-sensitive Detection of Human Pluripotent Stem Cells, Biomaterials, 2016, 105: 66-76.
(Continued)

*Primary Examiner* — Abdullahi Nur
(74) *Attorney, Agent, or Firm* — Emory Patent Group

(57) ABSTRACT

This disclosure relates to methods of detecting and quantifying low concentrations of cells in a sample with targeted nanoparticles having Raman reporters using surface-enhanced Raman scattering for detection. In certain embodiments, the sample is a group of cells derived from stem cells that have been differentiated into specific cell types and one is detecting residual stem cells or other progeny in order to quantify the purity of the sample. In certain embodiments, the targeted nanoparticles contain two or more Raman
(Continued)

reporters for the purpose of multiplexing. In certain embodiments, purity measurements are used to make quality control determinations.

13 Claims, 12 Drawing Sheets

(51) Int. Cl.
 C08G 65/334 (2006.01)
 G01N 21/65 (2006.01)
 G01N 33/569 (2006.01)
 G01N 33/58 (2006.01)

(52) U.S. Cl.
 CPC ..... *G01N 21/658* (2013.01); *G01N 33/56966* (2013.01); *G01N 33/588* (2013.01)

(56) References Cited

U.S. PATENT DOCUMENTS

| 10,137,208 | B2 | 11/2018 | Qian | |
|---|---|---|---|---|
| 2003/0211488 | A1 | 11/2003 | Mirkin | |
| 2009/0239217 | A1 | 9/2009 | Gibbs | |
| 2010/0068806 | A1 | 3/2010 | Laine | |
| 2011/0165077 | A1* | 7/2011 | Qian | A61K 49/0023 424/9.1 |
| 2011/0172523 | A1 | 7/2011 | Natan | |
| 2011/0281355 | A1 | 11/2011 | Xu | |
| 2013/0149247 | A1 | 6/2013 | Qian | |

OTHER PUBLICATIONS

Hentze et al. Teratoma formation by human embryonic stem cells: Evaluation of essential parameters for future safety studies, Stem Cell Research, 2009, 2, 198-210.

Israelsen et al. Nanoparticle Properties and Synthesis Effects on Surface-Enhanced Raman Scattering Enhancement Factor: An Introduction, The Scientific World Journal, 2015, Article ID 124582, 12 pages.

Lee et al. Tumorigenicity as a Clinical Hurdle for Pluripotent Stem Cell Therapies, Nat Med.,19(8):998-1004.

Pallaoro et al. Rapid Identification by Surface-Enhanced Raman Spectroscopy of Cancer Cells at Low Concentrations Flowing in a Microfluidic Channel, ACS Nano, 2015, 9(4):4328-36.

Qian et al. In vivo tumor targeting and spectroscopic detection with surface-enhanced Raman nanoparticle tags, Nat Biotechnol, 2008, 26(1):83-90.

Schopperle et al. The TRA-1-60 and TRA-1-81 Human Pluripotent Stem Cell Markers Are Expressed on Podocalyxin in Embryonal Carcinoma, Stem Cells, 2007, 25:723-730.

Stemcell, Anti-Human TRA-1-60 Antibody, Clone TRA-1-60R, Catalog No. #60064, 2017.

Tang et al. SSEA-5, an antibody defining a novel surface glycan on human pluripotent stem cells and its application to remove teratoma forming cells as part of a surface antibody panel, Nat Biotechnol, 29(9):829-834.

Tateno et al. Chapter 26 Live-Cell Imaging of Human Pluripotent Stem Cells by a Novel Lectin Probe rBC2LCN, in Lectins, Methods and Protocols, 2014, pp. 313-318.

Wang et al. Detection of Circulating Tumor Cells in Human Peripheral Blood using Surface-Enhanced Raman Scattering Nanoparticles, Cancer Res. 2011, 71(5):1526-32.

Yang et al. Ultrasensitive surface-enhanced Raman scattering detection in common fluids, Proc Natl Acad Sci U S A. 2016, 113(2):268-73.

* cited by examiner

FIG. 1B

METHODS OF MEASURING CELL PURITY FOR MAKING QUALITY CONTROL DETERMINATIONS AND RELATED COMPOSITIONS

CROSS-REFERENCE TO RELATED APPLICATIONS

This application is the National Stage of International Application No. PCT/US2016/038121 filed Jun. 17, 2016, which claims the benefit of priority to U.S. Provisional Application No. 62/182,012 filed Jun. 19, 2015. The entirety of each of these applications is hereby incorporated by reference for all purposes.

STATEMENT REGARDING FEDERALLY SPONSORED RESEARCH OR DEVELOPMENT

This invention was made with government support under Grant No. R21 HL123928 awarded by the National Institutes of Health. The government has certain rights in the invention.

BACKGROUND

There has been much interest in converting isolated stem cells into functioning tissues and organs through artificial laboratory procedures. For example, one can differentiate pluripotent stem cells (PSCs) into cardiac cells that spontaneously beat. However, the practical therapeutic use of these cells has been limited due to tumor formation. See Lee et al. Tumorigenicity as a clinical hurdle for pluripotent stem cell therapies. Nat. Med. 2013; 19: 998-1004. Residual stem cells or other progeny are thought to cause the tumor growth. Reports indicate that the number of residual stem cells sufficient to produce tumors in beating cardiac cells differentiated from human pluripotent stem cells (hPSCs) are at levels that cannot be detected using standard fluorescently tagged antibodies and FACS. Thus, there is a need to identify methods of detecting these cells at very low concentrations in order to make quality control determinations.

Raman spectroscopy directs electromagnetic radiation (e.g., in laser light source) on a molecule and detects scattered electromagnetic radiation of a changed wavelength. Plotting the intensity of shifted electromagnetic waves versus frequency is called a Raman spectrum. When a molecule is in close proximity to certain surfaces such as silver and gold nanoparticles, the intensity of scattered waves dramatically increases, a phenomenon referred to as surface-enhanced Raman scattering (SERS). Qian et al. report in vivo tumor targeting and spectroscopic detection with surface-enhanced Raman nanoparticle tags. Nature Biotechnology, 2008, 26, 83-90. Wang et al. report the detection of circulating tumor cells in human peripheral blood using surface-enhanced Raman scattering nanoparticles. Cancer Res. 2011, 71(5):1526-32. See also U.S. Pat. No. 7,588,827, and Published Patent Application Number 2013/0149247, 2010/0068806, and Isrealsen et al., Nanoparticle Properties and Synthesis Effects on Surface-Enhanced Raman Scattering Enhancement Factor: An Introduction, The Scientific World Journal, Volume 2015, Article ID 124582.

Pallaoro et al. report rapid identification by surface-enhanced Raman scattering of cancer cells at low concentrations flowing in a microfluidic channel. ACS Nano, 2015, 9 (4), pp 4328-4336.

Yang et al. report ultrasensitive surface-enhanced Raman scattering detection in common fluids. Proc Natl Acad Sci USA, 2016, 113:268-273. See also Yang et al. Chinese Patents CN 104387790 (2015) and CN 105199422 (2015).

References cited herein are not an admission of prior art.

SUMMARY

This disclosure relates to methods of detecting and quantifying low concentrations of cells in a sample with targeted nanoparticles having Raman reporters using surface-enhanced Raman scattering for detection. In certain embodiments, the sample is a group of cells derived from stem cells that have been differentiated into specific cell types and one is detecting residual stem cells or other progeny in order to quantify the purity of the sample. In certain embodiments, the targeted nanoparticles contain two or more Raman reporters for the purpose of multiplexing. In certain embodiments, purity measurements are used to make quality control determinations.

In certain embodiments, the disclosure relates to methods of detecting target cells in a sample comprising: mixing a sample comprising cells suspected of containing target cells having surface marker associated with the target cell with a nanoparticles, wherein the nanoparticles comprise: a) a metal, gold or silver core; b) a Raman reporter molecule positioned next to the surface of the gold or silver core; c) a layer of thiol polyethylene glycol encapsulating the Raman reporter molecule; and d) a specific binding agent capable of selectively binding with the target cell surface marker; wherein the mixing is done under conditions such that the specific binding agent binds the target cell surface marker providing nanoparticles bound to target cells; manipulating the sample under conditions such that nanoparticles not bound to target cells are separated from the sample providing a purified sample; exposing the purified sample to electromagnetic radiation providing scattering associated with the Raman reporter molecule; detecting an intensity of scattering associated with the Raman reporter molecule being exposed to the electromagnetic radiation indicating that the target cells are in the sample; and quantifying the number of target cells in the sample based on the intensity of scattering.

In certain embodiments, methods reported herein are used for quality control procedures. In certain embodiments, the quality control procedures comprise quantifying the number of target cells to provide a numerical measurement, wherein the numerical measurement above a threshold value when compared to the threshold value indicates the sample is not acceptable for use in a medical application or procedure or further processing or manipulations, and wherein the numerical measurement at or below a threshold value when compared to the threshold value indicates the sample is acceptable for use in a medical application or procedure or further processing or manipulations.

In certain embodiments, the number of target cells in the sample is quantified to be less than or between 0.01 or 0.005 or 0.001 or 0.0001 and a lower limit as a percentage of the total cells in the sample. In certain embodiments, the lower limit is $1\times10^{-4}$ or $1\times10^{-5}$, or $1\times10^{-6}$. In certain embodiments, the target cells or stem cells are pluripotent stem cells, induced pluripotent stem cells, or embryonic stem cells or progeny thereof.

In certain embodiments, the sample comprises cells that were differentiated from stem cells, pluripotent stem cells, induced pluripotent stem cells, or embryonic stem cells. In certain embodiments, the sample is a group of spontaneously beating cardiomyocytes derived from stem cells.

In certain embodiments, the specific binding agent is an antibody or mimetic that binds a stem cells surface marker.

In certain embodiments, the specific binding agent binds an H-1 and/or H-3 antigen such as an antibody thereto, e.g., anti-SSEA-5 or anti-TRA1-60 antibodies.

In certain embodiments, the specific binding agent is a pentameric immunoglobulin and the immunoglobulin density in the nanoparticle is between 15 and 150 or between 25 and 150 or between 50 and 150 antibodies per particle.

In certain embodiments, the specific binding agent is a pentameric immunoglobulin M (IgM) antibody and the thiol polyethylene glycol has an average molecular weight of between 15 and 25 kDa.

In certain embodiments, the specific binding agent is a monomeric immunoglobulin and the immunoglobulin density in the nanoparticle is between 15 and 60 or between 15 and 40 or between 15 and 30 antibodies per particle.

In certain embodiments, the specific binding agent is a monomeric immunoglobulin G (IgG) antibody and the thiol polyethylene glycol encapsulating the Raman reporter has an average molecular weight between 2 and 10 kDa.

In certain embodiments, the Raman reporter molecule is a thienyl-containing benzindole salt dyes such as (E)-2-(2-(5'-(dimethylamino)-2,2'-bithiophen-5-yl)vinyl)-1,1,3-trimethyl-1H-benzo[e]indolium iodide (BIDI), derivative or alternate salt thereof.

In certain embodiments, the nanoparticles comprise a first set of nanoparticles comprising a first specific binding agent and a first Raman reporter and a second set of nanoparticles comprising a second specific binding agent and a second Raman reporter, wherein the first Raman reporter and the second Raman reporter are not the same molecule and are configured such that exposing the purified sample to electromagnetic radiation result in a first scattering intensity associated with the first Raman reporter and a second scattering intensity associated with the second Raman reporter, wherein the first scattering intensity and the second scattering intensity are at different and distinct wavelengths.

In certain embodiments, the method further comprises detecting the first and second scattering intensity and quantifying the number of target cells in the sample based on the first and second scattering intensity.

In certain embodiments, the disclosure contemplates compositions comprising a nanoparticle, wherein the nanoparticles comprise: a) a gold or silver core; b) an Raman reporter molecule about the surface of the gold or silver core; c) a layer of thiol polyethylene glycol encapsulating the Raman reporter molecule; and d) a specific binding agent capable of selectively binding with a target cell surface marker.

BRIEF DESCRIPTION OF THE FIGURES

FIG. 1B schematically illustrates the preparation of Raman-encoded, PEG-stabilized, and SSEA-5-functionalized SERS nanoparticles.

DETAILED DISCUSSION

Figure 1A:
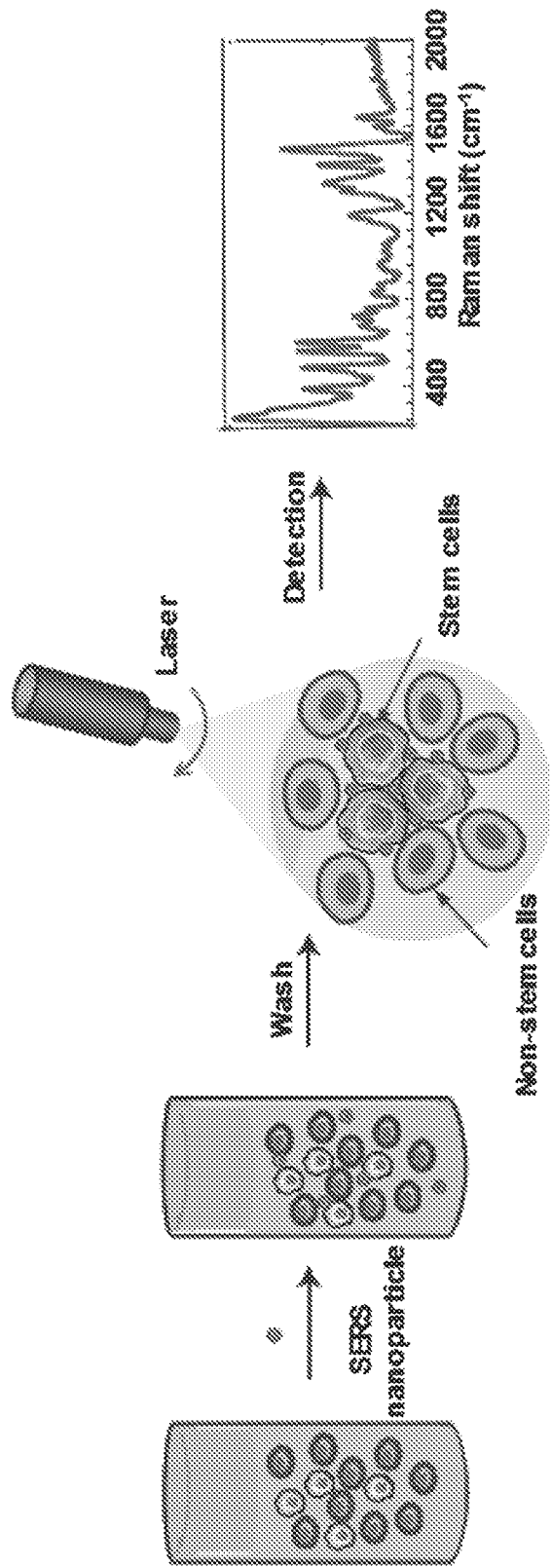
FIG. 1A shows a schematics of the SERS assay principle. A sample of cells are mixed with SERS nanoparticles functionalized with agents that specifically bind with cell surface markers. Excess unbound nanoparticles are washed and separated from the cells. The sample is subject to a laser scan and nanoparticle bound cells are detected based on scattering intensity changes in Raman spectrum.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise.

The terms "detecting", "measuring", "evaluating", "assessing," "assaying," and "analyzing" can be used interchangeably herein to refer to any form of measurement, and include determining if an element is present or not, and further quantifying calculations may be performed by comparing measured values to reference values. The process of comparing a measured value and a reference value can be carried out in any convenient manner appropriate to the type of measured value and reference value. Measuring can be performed using quantitative or qualitative measurement techniques, and the mode of comparing a measured value and a reference value can vary depending on the measurement technology employed. For example, the levels may be compared by visually comparing the intensity, or by comparing data from spectrometric measurements (e.g., comparing numerical data or graphical data, such as bar charts, derived from the measuring device). As with qualitative measurements, the comparison can be made by inspecting the numerical data, by inspecting representations of the data (e.g., inspecting graphical representations such as bar or line graphs).

The process of comparing may be manual or it may be automated. For example, a device for measuring electromagnetic radiation may include circuitry and software enabling it to compare a measured value with a reference value. Alternately, a separate device (e.g., a digital computer) may be used to compare the measured value(s) and the reference value(s).

As used herein, a "reference value" can be an absolute value; a relative value; a value that has an upper and/or lower limit; a range of values; an average value; a median value, a mean value, or a value as compared to a particular control or baseline value. A reference value can be based on an individual sample value, such as for example, a value obtained from a sample, but at an earlier point in time, or a value obtained from a sample with known properties. The reference value can be based on a large number of samples based on a pool of samples of known values including or excluding the sample to be tested.

As used herein the term "nanoparticles" refers to structures that have a size (maximum width or diameter) that is less than 1000 nm, typically less than 500 or 100 nm. Nanoparticles comprised of spherical gold cores are exemplified herein but other metals, materials, and shapes are contemplated. Examples include, but are not limited to, silver, organic polymers, silica, iron, iron oxide. In certain embodiments, the nanoparticles comprise a gold or silver shell with a core that is any material such as a gold shell over a silica core or silver-gold or gold-silver core-shell arrangements. When a Raman reporter molecule is about the surface of the gold or silver core the surface may be a gold or silver shell wherein the core is a different material. In certain embodiments, the shape is a nanorod. In certain embodiments the size is about 40 to 60 nm or between 20 to 100 or 30 to 100 nm.

Fluorescence activated cell-sorting (FACS) is method for identifying percentages of cell populations from a mixture. Cells are artificially made fluorescent based on the ability of a fluorescent probe, such as a tagged antibody, to specifically bind a molecule unique to the cell of interest. Distinct populations of fluorescent cells are separated and quantified based on techniques that take advantage of the unique fluorescent signature of each florescent probe bound cell. FACS typically accomplished by applying an electrical charge and separating by movement through an electrostatic field. Typically a vibrating mechanism causes a stream of cells to break into individual droplets. Just prior to droplet formation, cells in a fluid pass through an area for measuring fluorescence of the cell. An electrical charging mechanism is configured at the point where the stream breaks into droplets. Based on the fluorescence intensity measurement, a respective electrical charge is imposed on the droplet as it breaks from the stream. The charged droplets then move through an electrostatic deflection system that diverts droplets into areas based upon their relative charge. In some systems, the charge is applied directly to the stream, and the droplet breaking off retains charge of the same sign as the stream. In other systems, a charge is provided on a conduit inducing an opposite charge on the droplet.

Raman Spectroscopy and Surface Enhancement

If photons or other electromagnetic radiation hit a molecule, the photon may change direction or scatter. Sometimes the wavelength of the radiation also changes due to interactions with molecules referred to as Raman scattering, i.e., scattered photons which differ in frequency from the radiation source from which it was derived. Because the difference is related to vibrational and/or rotational properties of the molecules, the scattering pattern, such as intensity and changed frequency provide information on the molecular structure and environment. Plotting the intensity of shifted electromagnetic waves versus frequency is called a Raman spectrum. The direct measurement of a molecule using Raman spectroscopy results in acquisition of a unique spectrum of the molecular vibrations, referred to as the Raman signature. Thus, Raman spectroscopy can be using to detect molecules directly. Alternatively, one may also detect certain molecules indirectly by measuring the changes of a Raman spectrum associated with a Raman reporter after interacting with a target molecule.

The interaction of Raman reporters with surfaces such as silver, gold, copper, nickel, titanium, iron, or oxides or colloidal salts have be reported to enhance Raman scattering intensity, a phenomenon referred to as surface-enhanced Raman scattering (SERS). It is believed that morphology, size of the surface and the proximity of the surface to a Raman reporter influence the intensity of signals.

Raman reporters typically containing pi ($\pi$) bond electron systems such as those found in aromatics, heteroaromatics, and other conjugated configurations because as these molecules provide intense signals at certain wavelengths in the Raman spectrum. Raman reporters having a thienyl-containing benzindole salt dyes such as (E)-2-(2-(5'-(dimethylamino)-2,2'-bithiophen-5-yl)vinyl)-1,1,3-trimethyl-1H-benzo[e]indolium iodide (BIDI), oligo-azobenzenes bis-, tris-, or tetra-azobenzenes are exemplified herein, but other Raman reporters are contemplated such as, but not limited to, carboxyfluorescein (FAM), Rhodamine 6G (R6G), TRITC-DHPE, carboxy-X-rhodamine (ROX), BIODIPY TR-X, crystal violet (CV), malachite green (MG), malachite green isothiocyanate (MGITC), methylene blue, Cy5.5, Diethylthiatricarbocyanine iodide (DTTC) or derivatives thereof.

Methods of Measuring Purity for Quality Control Applications

This disclosure relates to methods of detecting and quantifying low concentrations of cells in a sample with targeted nanoparticles having Raman reporters using surface-enhanced Raman scattering for detection. In certain embodiments, the sample is a group of cells derived from stem cells that have been differentiated into specific cell types and one is detecting residual stem cells or other progeny in order to quantify the purity of the sample. In certain embodiments, the targeted nanoparticles contain two or more Raman reporters for the purpose of multiplexing.

In certain embodiments, the disclosure relates to methods of detecting target cells in a sample comprising: mixing a sample comprising cells suspected of containing target cells having surface marker associated with the target cell with a nanoparticles, wherein the nanoparticles comprise: a) a metal, gold or silver core; b) a Raman reporter molecule positioned next to the surface of the gold or silver core; c) a layer of thiol polyethylene glycol encapsulating the Raman reporter molecule; and d) a specific binding agent capable of selectively binding with the target cell surface marker; wherein the mixing is done under conditions such that the specific binding agent binds the target cell surface marker providing nanoparticles bound to target cells; manipulating the sample under conditions such that nanoparticles not bound to target cells are separated from the sample providing a purified sample; exposing the purified sample to electromagnetic radiation providing scattering associated with the Raman reporter molecule; detecting an intensity of scattering associated with the Raman reporter molecule being exposed to the electromagnetic radiation indicating that the target cells are in the sample; and quantifying the number of target cells in the sample based on the intensity of scattering.

In certain embodiments, methods reported herein use purity measurements to make quality control decisions. In certain embodiments, the quality control procedures comprise quantifying the number of target cells to provide a measurement, e.g., a numerical value, wherein the numerical measurement above a threshold value when compared to the threshold value indicates the sample is not acceptable for use in a medical application or procedure or further processing or manipulations, and wherein the numerical measurement at or below a threshold value when compared to the threshold value indicates the sample is acceptable for use in a medical application or procedure or further processing or manipulations.

In certain embodiments, the threshold value is 0.01 or 0.005 or 0.001 or 0.0001 percent of target cells for a sample, wherein the target cell is a stem cell, pluripotent stem cell, induced pluripotent stem cell, or embryonic stem cell derived product, such as cardiomyocytes.

In certain embodiments, the number of target cells in the sample is quantified to be less than or between 0.01 or 0.005 or 0.001 or 0.0001 and a lower limit as a percentage of the total cells in the sample. In certain embodiments, the lower limit is $1\times10^{-4}$ or $1\times10^{-5}$, or $1\times10^{-6}$. In certain embodiments, the target cells or stem cells are circulating tumor cells, pluripotent stem cells, induced pluripotent stem cells, or embryonic stem cells or progeny thereof.

In certain embodiments, the sample is a stem cell derived product or human blood cells.

The term "target cells" refers to cells that contain a cell surface marker for which the targeting agent specifically binds (specific binding agent). The term "specific binding agent" or "targeting agent" refers to a molecule, preferably a proteinaceous molecule that binds the cells surface marker with a greater affinity than proteins generally. Typically the specific binding agent is an antibody, such as a polyclonal antibody, a monoclonal antibody (mAb), a chimeric antibody, a CDR-grafted antibody or mimetic. Typical targeting agents are antibodies that specifically binds cell markers. SSEA-5 antibodies and TRA1-60 antibodies are exemplified herein, but other targeting agents that specifically bind cell markers are contemplated such as antibodies to tumor cell markers. The SSEA-5 antibody binds a carbohydrate antigen with a terminal presentation of the carbohydrate motif Fuc1-2Galβ1-3GlcNAcβ (H type-1 (H-1) antigen). See Tang et al. Nature Biotechnology, 29, 829-834 (2011). Thus, in certain embodiments, this disclosure contemplates the use of any specific binding agent that binds the H-1 antigen (Fuc.alpha.2Gal.beta.3GlcNAc) epitope such as any of the commercially available antibody sources (antibody of clone 17-206 (ab3355) by Abcam) or modifications therefrom using routine methods for their preparation.

The TRA-1-60 antibody is known to specifically recognize a carbohydrate epitope on glycoprotein podocalyxin. A pluripotent stem cell-specific lectin probe, recombinant N-terminal domain of BC2L-C (rBC2LCN), also recognizing glycosylated cell surface podocalyxin. rBC2LCN binds terminal H-type 1 trisaccharide (αFuc1-2βGal1-3βGlcNAc) and H-type 3 trisaccharide (αFuc1-2βGal1-3αGalNAc). Thus, in certain embodiments, this disclosure contemplates the use of any specific binding agent that binds the H-1 and/or H-3 antigen such as any of the commercially available antibody sources or using routine methods for their preparation.

Examples of specific binding agents include antibodies or mimetics that specifically bind glycan or protein sequences of other cell markers such as, but not limited to, SSEA-1, SSEA-3, SSEA-4, Tra-1-81, stem cells antigen-1, stem cell factor, P-glycoprotein ABCB5, LNGFR, CDw338, CD117, CD105, CD133, CD166, CD29, CD30, CD31, CD33, CD34, CD44, CD45, CD56, CD73, CD9, CD90, CD318, CD24, CD309, CD243, Chondroitin sulfate proteoglycan 4, hepatocyte growth factor receptor (HGFR). Using agents that specifically bind to combinations of the cell markers are contemplated for multiplexing. In certain embodiments, a combination of two or more specific binding agents selectively bind SSEA-5, CD9, CD30, CD50, CD90, CD200. See Tang et al. SSEA-5, an antibody defining a novel surface glycan on human pluripotent stem cells and its application to remove teratoma-forming cells as part of a surface antibody panel. Nat Biotechnol, 2011, 29(9): 829-834.

The specific binding agents of the present disclosure, such as the antibodies, antibody fragments, and antibody derivatives of the disclosure can further comprise any constant region known in the art. The light chain constant region can be, for example, a kappa- or lambda-type light chain constant region, e.g., a human kappa- or lambda-type light chain constant region. The heavy chain constant region can be, for example, an alpha-, delta-, epsilon-, gamma-, or mu-type heavy chain constant regions, e.g., a human alpha-, delta-, epsilon-, gamma-, or mu-type heavy chain constant region. In one embodiment, the light or heavy chain constant region is a fragment, derivative, variant, or mutant of a naturally occurring constant region.

In one embodiment, the specific binding agents of the present disclosure, such as the antibodies, antibody fragments, and antibody derivatives of the disclosure comprise an IgG or IgM. Techniques are known for deriving an antibody of a different subclass or isotype from an antibody of interest, i.e., subclass switching. Thus, IgG antibodies may be derived from an IgM antibody, for example, and vice versa. Such techniques allow the preparation of new antibodies that possess the antigen-binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g., DNA encoding the constant domain of an antibody of the desired isotype. See also Lantto et al., 2002, Methods Mol. Biol. 178:303-16.

The specific binding agents of the present disclosure, such as the antibodies, antibody fragments, and antibody derivatives of the disclosure may comprise the IgG1 heavy chain constant domain or a fragment of the IgG1 heavy chain domain. The antibodies, antibody fragments, and antibody derivatives of the disclosure may further comprise the constant light chain kappa or lambda domains or a fragment of these. Light chain constant regions and polynucleotides encoding them are provided herein below. In another embodiment, the antibodies, antibody fragments, and antibody derivatives of the disclosure further comprise a heavy chain constant domain, or a fragment thereof, such as the IgG2 heavy chain constant region.

The disclosure further embraces derivative specific binding agents or antibodies covalently modified to include one or more water soluble polymer attachments optionally thiol terminated such as thiol polyethylene glycol, polyoxyethylene glycol, or polypropylene glycol as described U.S. Pat. Nos. 4,640,835, 4,496,689, 4,301,144, 4,670,417, 4,791,192 and 4,179,337. Still other useful polymers known in the art include monomethoxy-polyethylene glycol, dextran, cellulose, or other carbohydrate based polymers, poly-(N-vinyl pyrrolidone)-polyethylene glycol, propylene glycol homopolymers, a polypropylene oxide/ethylene oxide co-polymer, polyoxyethylated polyols (e.g., glycerol) and polyvinyl alcohol, as well as mixtures of these polymers. Particularly preferred are specific binding agent products covalently modified with thiol terminated polyethylene glycol (PEG) subunits. Water-soluble polymers may be bonded at specific positions, for example at the amino terminus of the specific binding agent products, or randomly attached to one or more side chains of the polypeptide.

Numerous methods known to those skilled in the art are available for obtaining antibodies or antigen-binding fragments thereof. For example, antibodies can be produced using recombinant DNA methods (U.S. Pat. No. 4,816,567). Monoclonal antibodies may also be produced by generation of hybridomas in accordance with known methods. Hybridomas formed in this manner are then screened using standard methods, such as enzyme-linked immunosorbent assay (ELISA) and surface plasmon resonance analysis, to identify one or more hybridomas that produce an antibody that specifically binds with a specified antigen. Any form of the specified antigen may be used as the immunogen, e.g., recombinant antigen, naturally occurring forms, any variants or fragments thereof, as well as antigenic peptide thereof.

The modular structure of antibodies makes it possible to remove constant domains in order to reduce size and still retain antigen-binding specificity. Engineered antibody fragments allow one to create antibody libraries. A single-chain antibody (scFv) is an antibody fragment where the variable domains of the heavy (VH) and light chains (VL) are combined with a flexible polypeptide linker. The scFv and Fab fragments are both monovalent binders but they can be engineered into multivalent binders to gain avidity effects. One exemplary method of making antibodies and fragments includes screening protein expression libraries, e.g., phage or ribosome display libraries. Phage display is described, for example, in U.S. Pat. No. 5,223,409.

In addition to the use of display libraries, the specified antigen can be used to immunize a non-human animal, e.g., a rodent, e.g., a mouse, hamster, or rat. In one embodiment, the non-human animal includes at least a part of a human immunoglobulin gene. For example, it is possible to engineer mouse strains deficient in mouse antibody production with large fragments of the human Ig loci. Using the hybridoma technology, antigen-specific monoclonal antibodies derived from the genes with the desired specificity may be produced and selected. See U.S. Pat. No. 7,064,244.

Antibody mimetics or engineered affinity proteins are polypeptide based target binding proteins that can specifically bind to targets but are not specifically derived from antibody VH and VL sequences. Typically, a protein motif is recognized to be conserved among a number of proteins. One can artificially create libraries of these polypeptides with amino acid diversity and screen them for binding to targets through phage, yeast, bacterial display systems, cell-free selections, and non-display systems. See Gronwall & Stahl, J Biotechnology, 2009, 140(3-4), 254-269, hereby incorporated by reference in its entirety. Antibody mimetics include affibody molecules, affilins, affitins, anticalins, avimers, darpins, fynomers, kunitz domain peptides, and monobodies.

Affibody molecules are based on a protein domain derived from staphylococcal protein A (SPA). SPA protein domain denoted Z consists of three α-helices forming a bundle structure and binds the Fc protion of human IgG1. A combinatorial library may be created by varying surface exposed residues involved in the native interaction with Fc. Affinity proteins can be isolated from the library by phage display selection technology. See Orlova et al., Cancer Res., 2007, 67:2178-2186, hereby incorporated by reference in its entirety. Orlova et al. report a HER2 binding affibody with picomolar affinity. Molecule Cancer Res. 2006, 66:4339.

Monobodies, sometimes referred to as adnectins, are antibody mimics based on the scaffold of the fibronectin type III domain (FN3). See Koide et al., Methods Mol. Biol. 2007, 352: 95-109, hereby incorporated by reference in its entirety. FN3 is a 10 kDa, β-sheet domain that resembles the VH domain of an antibody with three distinct CDR-like loops, but lack disulfide bonds. FN3 libraries with randomized loops have successfully generated binders via phage display (M13 gene 3, gene 8; T7), mRNA display, yeast display and yeast two-hybrid systems. See Bloom & Calabro, Drug Discovery Today, 2009, 14(19-20):949-955, hereby incorporated by reference in its entirety.

Anticalins, sometimes referred to as lipocalins, are a group of proteins characterized by a structurally conserved rigid β-barrel structure and four flexible loops. The variable loop structures form an entry to a ligand-binding cavity. Several libraries have been constructed based on natural human lipocalins, i.e., ApoD, NGAL, and Tlc. See Skerra, FEBS J., 275 (2008), pp. 2677-2683, hereby incorporated by reference in its entirety.

The ankyrin repeat (AR) protein is composed repeat domains consisting of a β-turn followed by two α-helices. Natural ankyrin repeat proteins normally consist of four to six repeats. The ankyrin repeats form a basis for darpins (designed ankyrin repeat protein), which is a scaffold comprised of repeats of an artificial consensus ankyrin repeat domain. Combinatorial libraries have been created by randomizing residues in one repeat domain. Different numbers of the generated repeat modules can be connected together and flanked on each side by a capping repeat. The darpin libraries are typically denoted NxC, where N stands for the N-terminal capping unit, C stands for the C-terminal capping domain and x for the number of library repeat domains, typically between two to four. See Zahnd et al., J. Mol. Biol., 2007, 369:1015-1028, hereby incorporated by reference in its entirety.

Aptamers refer to affinity binding molecules identified from random proteins or nucleic acid libraries. Peptide aptamers have been selected from random loop libraries displayed on TrxA. See Borghouts et al., Expert Opin. Biol. Ther., 2005, 5:783-797, hereby incorporated by reference in its entirety. SELEX ("Systematic Evolution of Ligands by Exponential Enrichment") is a combinatorial chemistry technique for producing oligonucleotides of either single-stranded DNA or RNA that specifically bind to a target. Standard details on generating nucleic acid aptamers can be found in U.S. Pat. No. 5,475,096, and U.S. Pat. No. 5,270,163. The SELEX process provides a class of products, which are referred to as nucleic acid ligands or aptamers, which has the property of binding specifically to a desired target compound or molecule. Each SELEX-identified nucleic acid ligand is a specific ligand of a given target compound or molecule. The SELEX process is based on the fact that nucleic acids have sufficient capacity for forming a variety of two- and three-dimensional structures and sufficient chemical versatility available within their monomers to act as ligands (form specific binding pairs) with virtually any chemical compound, whether monomeric or polymeric.

EXAMPLES

Surface-Enhanced Raman Scattering-based Assays for Detection of hPSCs

An assay was developed using SERS nanoparticles targeting two stem cell surface markers SSEA-5 and TRA1-60 individually or simultaneously (FIG. 1A). The assays has high specificity for detecting residual hPSCs in a sample and sensitivity of the assay was several orders of magnitude higher than the sensitivity of flow cytometry assays (0.0001% to 0.0006% vs. ~0.2% to 1.2%). Using the SERS assay, it was determine that the purity of cardiomyocyte in the form of 3D spheres obtained from differentiation cultures had reduced levels of residual SSEA-5+ and TRA1-60+ cells when compared cardiomyocytes differentiated in parallel 2D cultures.

Compared to other methods for examining residual cells in differentiated cultures such as flow cytometry or teratoma testing, the SERS based assays have several desirable attributes, including highly sensitive, fast and easy to use, and amenable to quality control assay for hPSC-derived products. In addition, the SERS based assays disclosed herein facilitate safety assessment of cell preparations for transplantations that require large doses of cells, which is unachievable using flow cytometry or teratoma testing in mice.

Successfully establishing SERS based assays with ultrahigh sensitivity required fine tuning several elements during the preparation of nanoparticles and overall assay design. The PEG layer and ligand density significantly affect the relative SERS signal. PEG coatings are used to protect the Raman reporter from the biological environment and keep the reporter locked to the nanoparticle surface in order to preserve SERS intensities and stability. Experiments reported herein indicate that a PEG-SH with higher MW was optimal for TRA1-60 (IgM) SERS nanoparticles. The nanoparticles with PEG-SH-20k had 26-fold increased relative SERS signals compared with those with PEG-SH-5k.

The SERS assays enabled labeling and detection of a trace amount of cells that express stem cell markers either SSEA-5 or TRA1-60 pluripotency markers. SSEA-5 is an antigen which is highly and specifically expressed on hPSCs. TRA1-60 is also surface marker associated with undifferentiated hPSCs. It is possible that monitoring multiple markers is required in order to assure the safety of hPSC-derived products since tumor formation from these cell products are complex. Tumors can be derived from residual undifferentiated cells but hypothetically it may also be caused by malignant transformation of differentiated or partially differentiated cells or progenitors that have high proliferative capacity. Correspondingly, the strategy to increase safety is to assure the absence of undifferentiated cells or other partially differentiated cell that could initiate tumor formation and develop methods to selectively eliminate residual stem cells.

With the anticipation that measurements of multiple markers are needed to be able to accurately predict the tumorigenic potential of hPSC-derived products, the SERS assays may be used in combination with other methods such as PCR to detect target cells. For example, it is contemplated that the SERS based assay be used in combination with qRT-PCR analysis of LIN28 to detect residual undifferentiated hPSCs.

Preparation and Optimization of SSEA-5- or TRA1-60-SERS Nanoparticles

In order to specifically detect residual stem cells, two SERS nanoparticles functionalized with antibodies targeting stem cell surface markers, SSEA-5 and TRA1-60 were developed. Both markers are specific to pluripotent stem cells and are reported to be useful for delineating undifferentiated cells from differentiated cells. FIG. 1A illustrates an assay using SERS nanoparticles for labeling and detecting rare stem cells. After staining and washing a sample of cells suspected of containing residual stem cells, the level of stem cells bonded with SERS nanoparticles is detected using Raman spectroscopy.

The following chemicals were used 60 nm citrate-stabilized gold particles ($2.6 \times 10^{10}$ particles/mL) (Ted Pella Inc); black hole quencher dye (BHQ) (Biosearch Technologies), mPEG-SH (MW=2,000, 5,000, 10,000, and 20,000 Da) (Rapp Polymere, Germany), SSEA-5 IgG1 antibody (Stemcell Technologies), TRA1-60 IgM antibody (Millipore).

The compound (E)-2-(2-(5'-(dimethylamino)-2,2'-bithiophen-5-yl)vinyl)-1,1,3-trimethyl-1H-benzo[e]indolium iodide (BIDI) with the following structure,

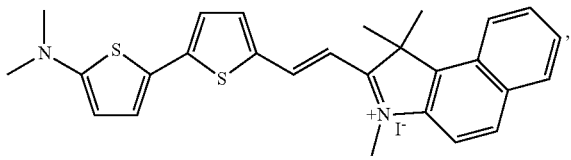 [SMILES: CN(C)c1ccc(-c2ccc(/C=C/C3=[N+](C)c4ccc5ccccc5c4C3(C)C)s2)s1 ; [I-]]

was prepared according to the procedures provided in Chinese Patent CN 104387790 (2015).

$^1$HNMR (DMSO, 500MHz): δ=8.61-8.64(d, 1H, $C_{10}H_6$), 8.36-8.38 (d, 1H, $C_{10}H_6$), 8.21-8.23(d, 1H, $C_2H_2$), 8.15-8.17 (d, 1H, $C_{10}H_6$), 8.04-8.05 (d, 1H, $C_4H_2S$), 7.97-7.99(1, H, $C_2H_2$), 7.74-7.77(m, 1H, $C_{10}H_6$), 7.63-7.66 (m, 1H, $C_{10}H_6$), 7.56-7.57(d, 1H, $C_4H_2S$), 7.37-7.38 (d, 1H, $C_4H_2S$), 6.84-6.87 (d, 1H, $C_{10}H_6$), 6.16-6.17 (d, 1H, $C_4H_2S$), 4.05(s, 3H, $CH_3$), 3.08(s, 6H, $CH_3$), 1.98(s, 6H, $CH_3$). MALDI-TOF-MS: m/z433.0 (M−I$^−$).

Figure 1B:
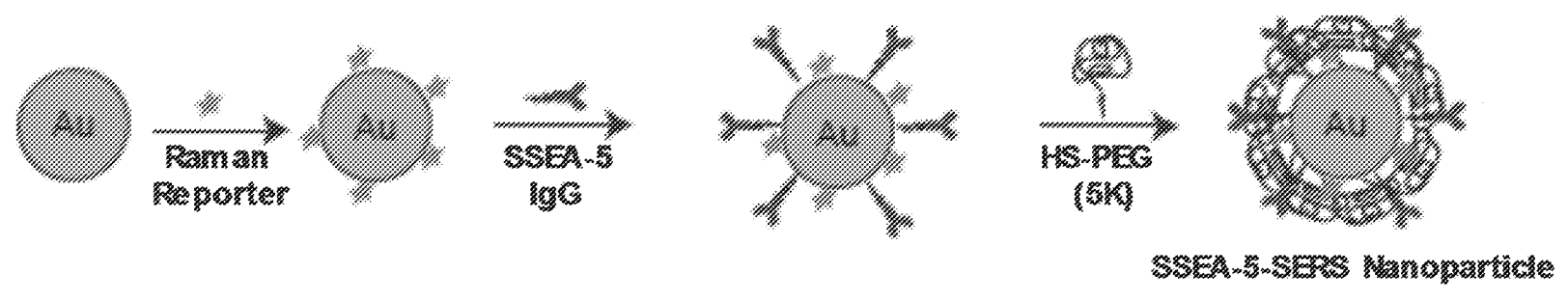
Figure 1C:
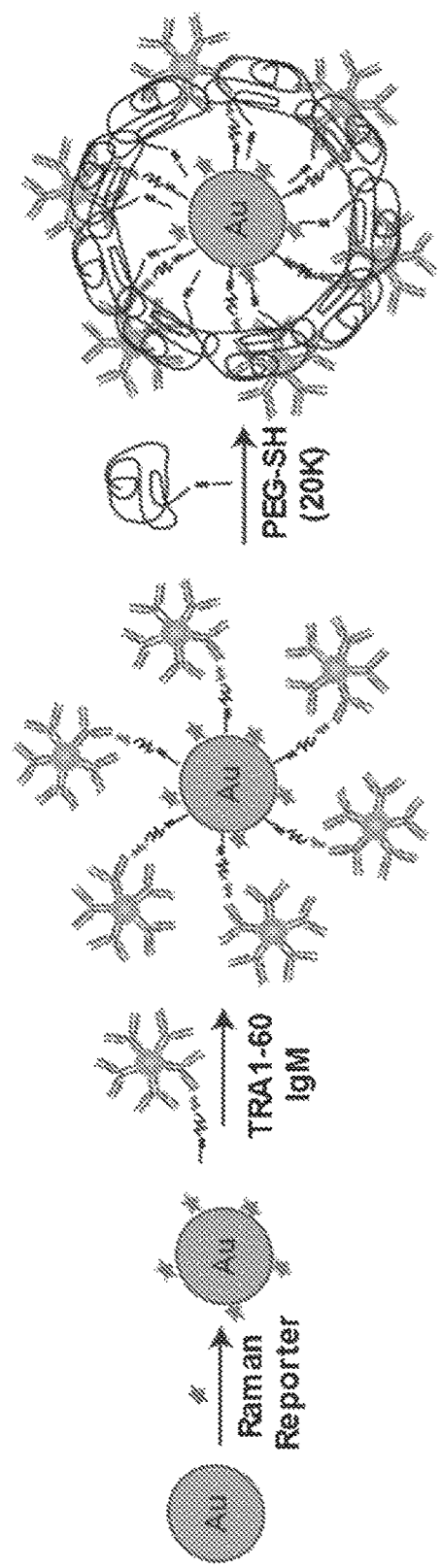
FIG. 1C schematically illustrates the preparation of Raman-encoded, PEG-stabilized, and TRA-1-60-functionalized SERS nanoparticles.
Figure 2A:
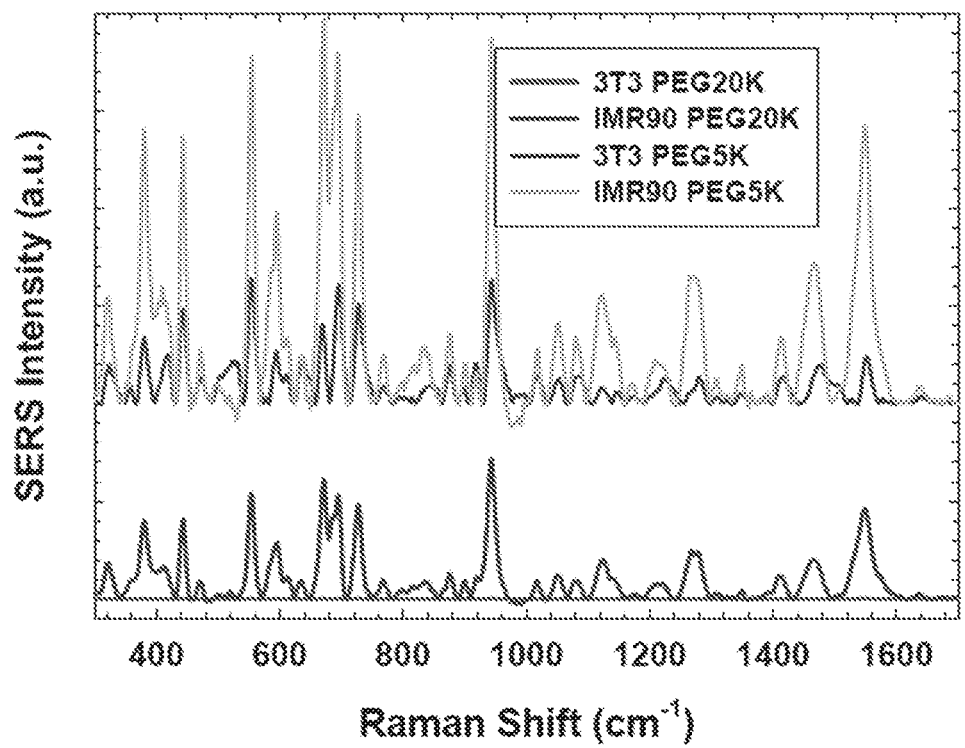
FIG. 2A shows SERS signals of PEG20k- and PEG5k-stabilized TRA1-60-SERS nanoparticles in IMR-90 iPSCs or NIH3T3 fibroblasts.
Figure 2B:
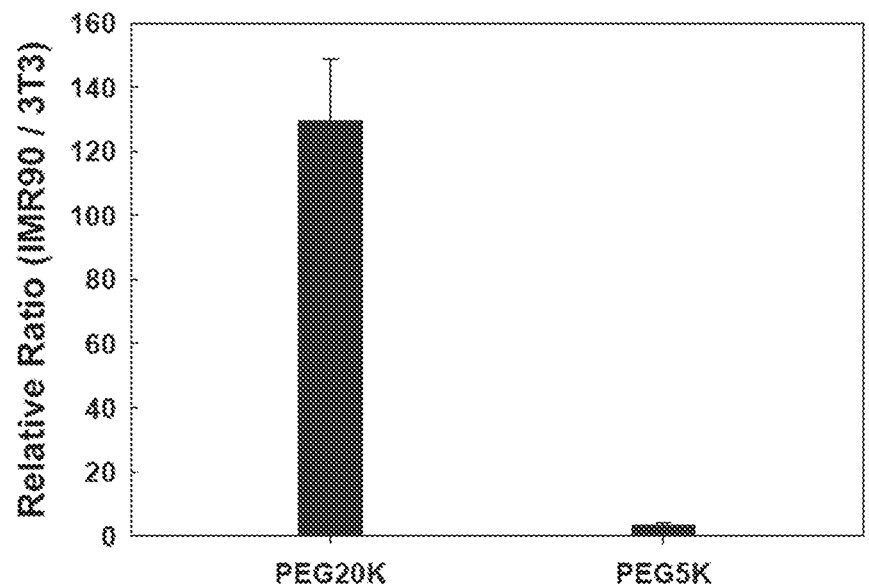
FIG. 2B shows the relative SERS signal ratios of PEG20k- vs. PEG5k-stabilized TRA1-60 SERS nanoparticles in targeting IMR-90 iPSCs vs. NIH3T3 fibroblasts.
Figure 3A:
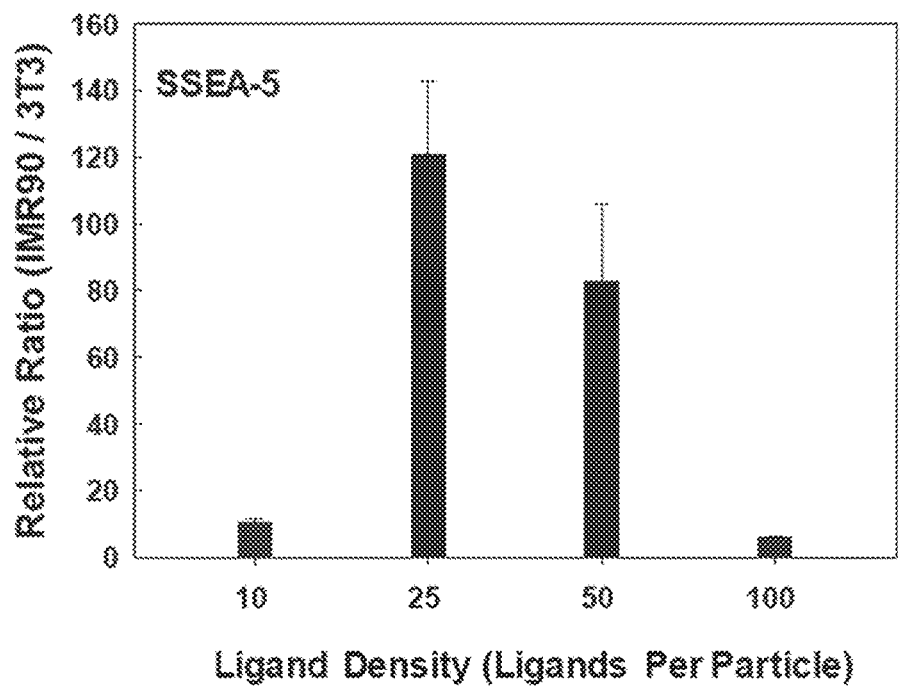
FIG. 3A shows data on the modifications of anti-SSEA-5 IgG density of SERS nanoparticles. Effect of the ligand density on the relative SSEA-5-SERS signals targeting IMR-90 iPSCs vs. NIH3T3 fibroblasts. A ligand density of 25 antibodies per particle in SSEA-5-SERS produced the highest signal ratio.
Figure 3B:
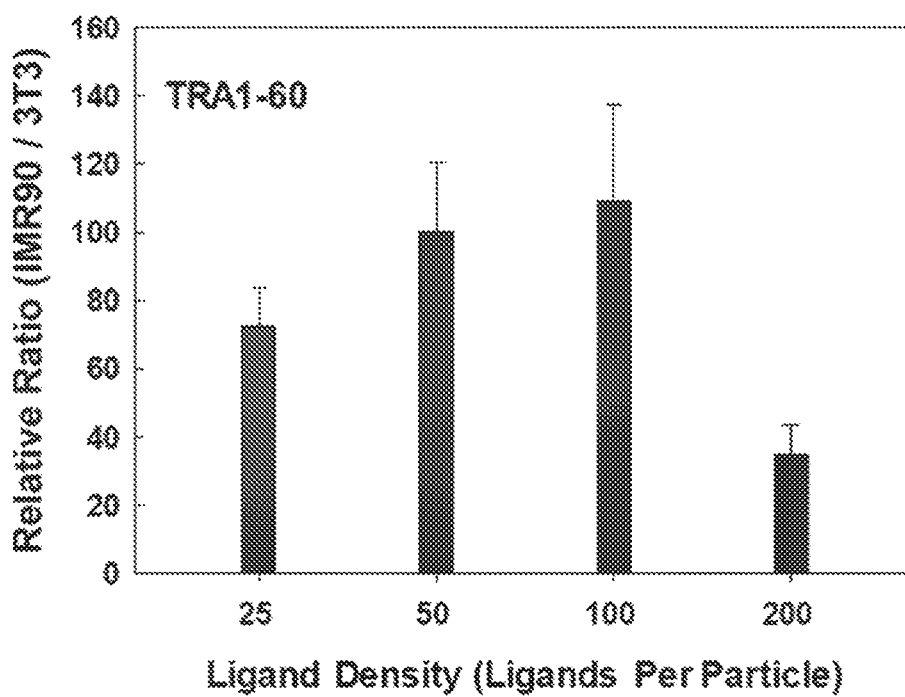
FIG. 3B shows data on the effect of the ligand density on the relative TRA1-60-SERS signals targeting IMR-90 iPSCs vs. NIH3T3 fibroblasts. A ligand density of 100 antibodies per particle in TRA1-60-SERS produced the highest signal ratio.

SSEA-5 (IgG1) or TRA1-60 (IgM) antibody-conjugated SERS nanoparticles were prepared through several steps including Raman encoding, polyethylene-glycol (PEG) stabilization, and antibody conjugation (FIGS. 1B and 1C). The nanoparticles were optimized in order to obtain high relative SERS signal, i.e., the SERS signal ratio of positive and negative cells. Due to significant differences in the size and structure of SSEA-5 (IgG1) and TRA1-60 (IgM) antibodies, a two-step approach was applied to optimize the SERS nanoparticles by first modifying the PEG stabilizing layer and then titrating the ligand density. In the first step, the effect of the length of PEG layers on relative SERS signal ratios of IMR-90 iPSCs (positive cells) and NIH3T3 fibroblasts (negative cells) was evaluated. For TRA1-60 (IgM)-SERS nanoparticles, the length of the PEG-SH needed to be increased to stabilize the TRA1-60-SERS nanoparticles, likely due to the pentamer structure of IgM (FIG. 1C). PEG-SH with MW 20,000 Da (PEG-SH-20k) generated relative SERS signal at ~130, which was ~26-fold higher compared with those of PEG-SH-5k (FIG. 2A). In the second step, the effect of the ligand/antibody density on the relative SERS signal of the nanoparticles was evaluated. For SSEA-5-SERS nanoparticles, the relative SERS signal of the nanoparticles with a ligand density of 25 antibodies per particle was the highest among all nanoparticles with various ligand densities tested (FIG. 3A). For TRA1-60-SERS nanoparticles, the highest relative SERS signal was detected by the nanoparticles with a ligand density of 100 antibodies per particle (FIG. 3B). Thus, the ligand densities of 25 and 100 antibodies per particle were selected for the preparation of nanoparticles conjugated with SSEA-5 and TRA1-60 antibodies, respectively.

Figure 4A:
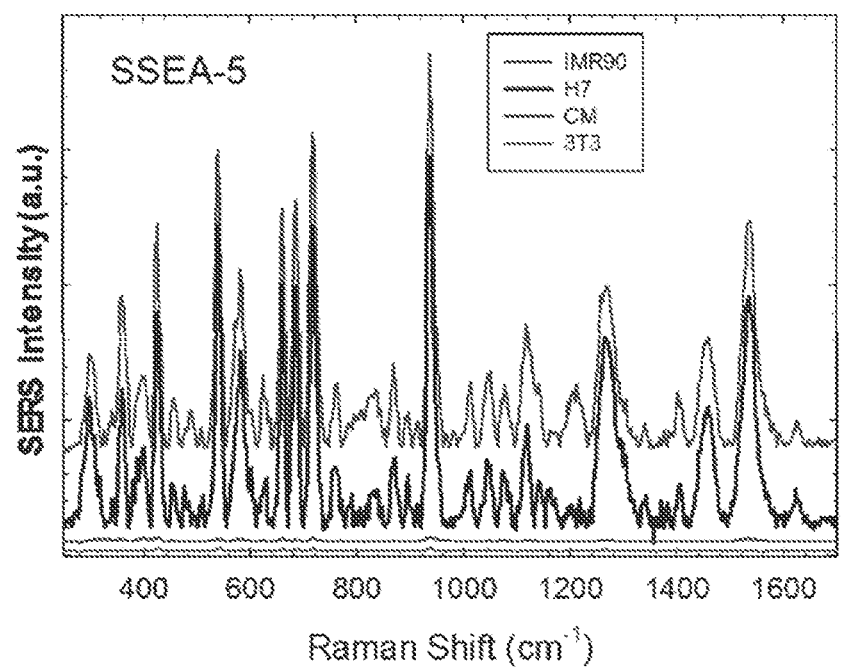
FIG. 4A shows data indicating that the SERS assays can detect hPSCs specifically using SSEA-5-SERS nanoparticles. SERS signals of SSEA-5-SERS nanoparticles were detected in pluripotent stem cells, IMR-90 iPSCs (top) or H7 hESCs (below), but not in non-stem cells NIH3T3 fibroblasts (3T3, bottom), and primary rat cardiomyocytes (CM, above).
Figure 4B:
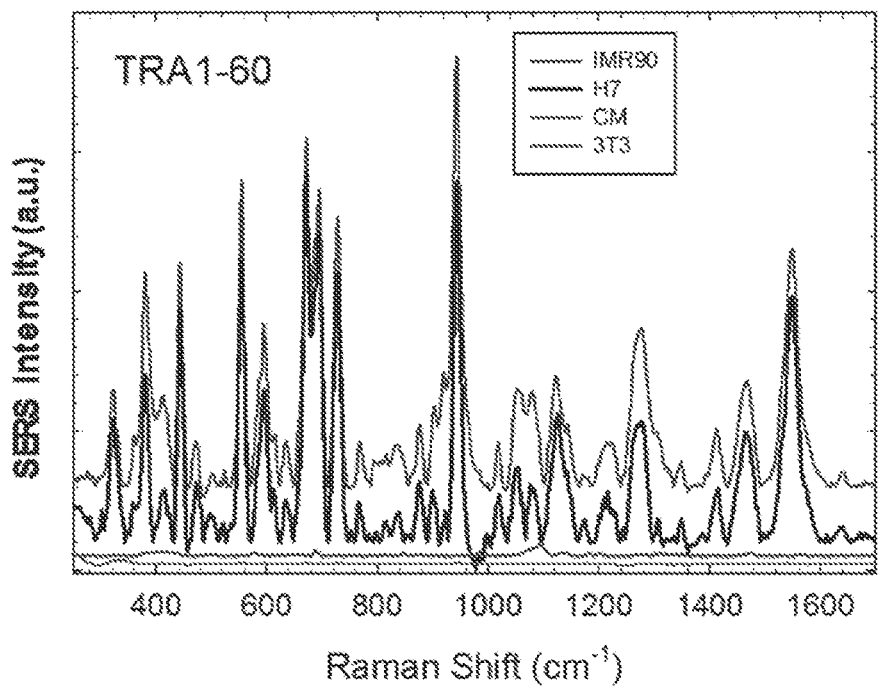
FIG. 4B shows data for TRA-1-60-SERS.
Figure 4C:
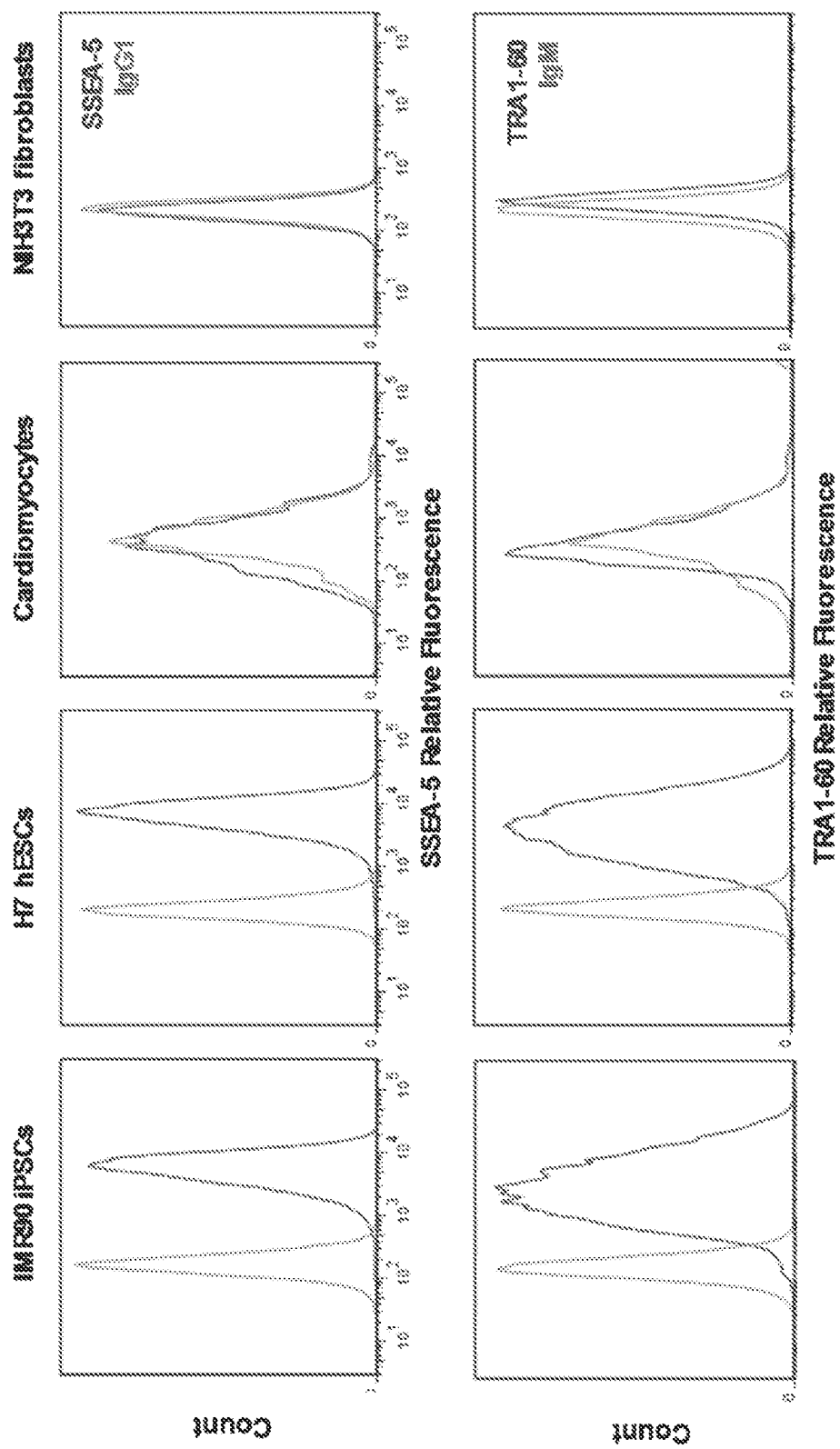
FIG. 4C shows data on flow cytometry analysis of pluripotent stem cell surface markers. SSEA-5+ or TRA-1-60+ were detected in IMR-90 iPSCs and H7 hESCs, but not in cardiomyocytes and NIH3T3 fibroblasts.

Development of SERS Assays Targeting Individual Surface Markers: Specificity and Sensitivity The specificity of SSEA-5- or TRA1-60-SERS nanoparticles was assessed using cells with (IMR-90 iPSCs and H7 hESCs) or without (primary cardiomyocytes and NIH3T3 fibroblasts) these specific surface markers. After cells were incubated with SSEA-5- or TRA1-60-SERS nanoparticles, strong SERS signals were detected only in pluripotent stem cells with these surface markers, and not in non-stem cells without these surface markers (FIGS. 4A and 4B), suggesting specific bindings of these two SERS nanoparticles to pluripotent stem cells. SERS nanoparticles conjugated with corresponding isotype controls (IgG1 or IgM) also displayed negligible SERS signals for all cell lines. Flow cytometry analysis indicated that SSEA-5 and TRA1-60 were specifically expressed on IMR-90 iPSCs and H$_7$ hESCs, but not on cardiomyocytes and fibroblasts (FIG. 4C). Therefore, both SSEA-5- or TRA1-60-SERS nanoparticles specifically detected pluripotent stem cells.

Figure 5A:
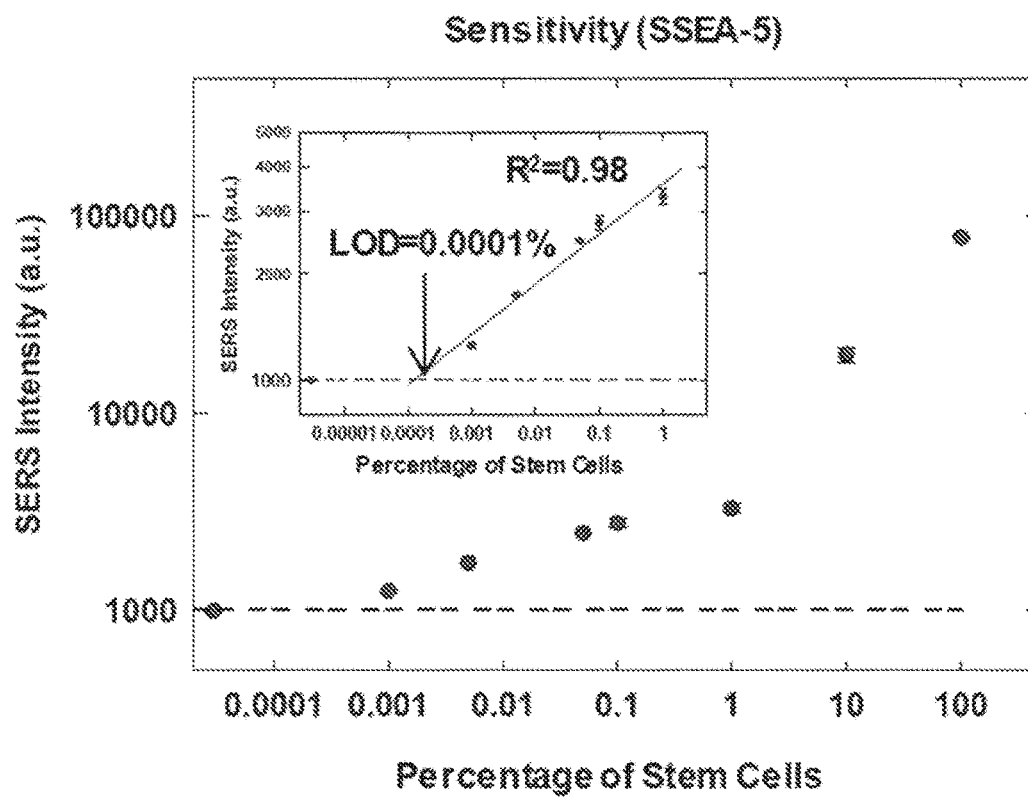
FIG. 5A shows data indicating the SERS assays are highly sensitive. The correlation between the relative SSEA-5-SERS intensity and the amount of stem cells in cell preparations generated by mixing hPSCs with NIH3T3 fibroblasts. The LOD, limit of detection, was determined by mean signal detected in NIH3T3 cells plus three times of the standard deviation of measurements of NIH3T3 cells.
Figure 5B:
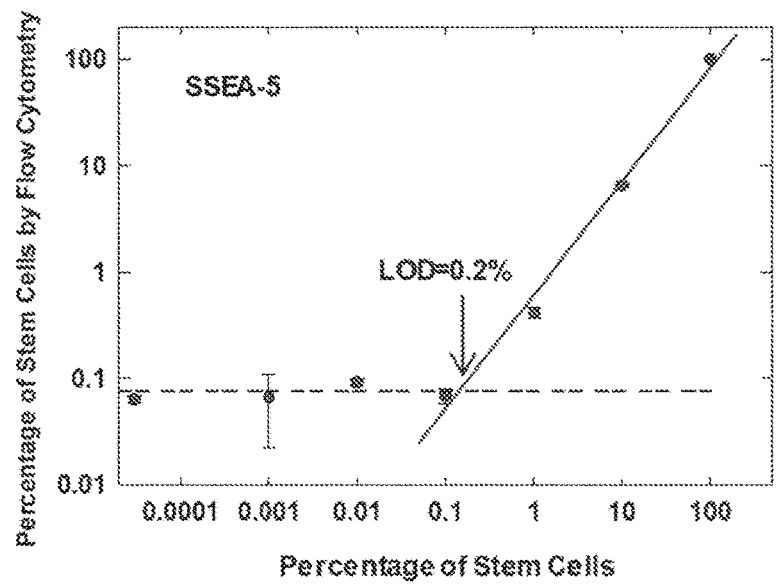
FIG. 5B shows the correlation between the percentage of SSEA-5+ cells detected by flow cytometry analysis and the amount of stem cells in cell preparations generated by mixing hPSCs with NIH3T3 fibroblasts.

To determine the sensitivity of these SERS assays, cell preparations were generated containing various amounts of hPSCs by mixing hPSCs with NIH3T3 fibroblasts. Each cell preparation was then analyzed with SSEA-5- or TRA1-60-SERS nanoparticles. The SERS signal intensity detected by both SSEA-5- and TRA1-60-SERS assays was positively correlated with the number of stem cells (FIG. 5A). For samples containing ≤1% stem cells, the SERS signal intensity displayed linear correlation with the number of hPSCs (R2=0.99, FIG. 5A, insets). The limit of detection (LOD) was 0.0001% SSEA-5+ or 0.0001% TRA1-60+ stem cells (i.e., 1 stem cell in a background of $10^6$ cells). In contrast, the estimated LOD for flow cytometry analysis was 0.2% SSEA-5+ or 1.5% TRA1-60+ stem cells (i.e., 2000 or 15,000 stem cells in a background of $10^6$ cells) (FIG. 5B). Therefore, the sensitivity of the SERS assays was ~2,000 to 15,000-fold higher than that of flow cytometry assays.

Development of a Multiplexing SERS Assay: Specificity and Sensitivity

Figure 6A:
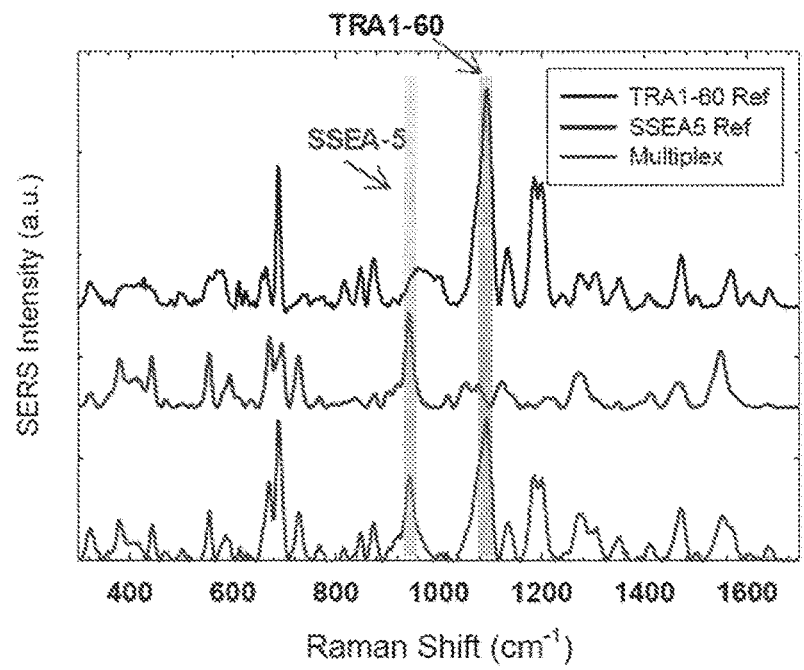
FIG. 6A shows Raman shift signal intensity using the multiplexing SERS assay. SSEA-5-SERS nanoparticles and TRA-1-60-SERS nanoparticles were generated using Raman reporters with distinct SERS spectrum patterns. In the multiplexing assays, SERS signals from SSEA-5-SERS nanoparticles and TRA-1-60-SERS nanoparticles were detected simultaneously in the combined SERS spectra using their unique SERS signals at specific spectral regions, marked by first and second bars, left to right respectively.

It was examined whether SSEA-5+ and TRA1-60+ cells could be detected simultaneously in a multiplexing assay using nanoparticles with distinct SERS spectral patterns. SSEA-5 antibodies were conjugated with SERS nanoparticles encoded with the BIDI reporter and TRA1-60 antibodies with SERS nanoparticles encoded with the black hole quencher dye (BHQ) reporter. These nanoparticles emitted SERS signals at the same spectral region of 200-1,800 cm-1 when they were simultaneously excited with a single laser bean at 785 nm (FIG. 6A). After stem cells were labeled with these nanoparticles, the final SERS spectra detected in the multiplexing assay was a combination of two distinct SERS spectral patterns (FIG. 6A). Signals from SSEA-5 and TRA1-60-SERS nanoparticles were distinguished using their unique SERS signals at different spectral regions (marked right to left respectively, FIG. 6A).

Figure 6B:
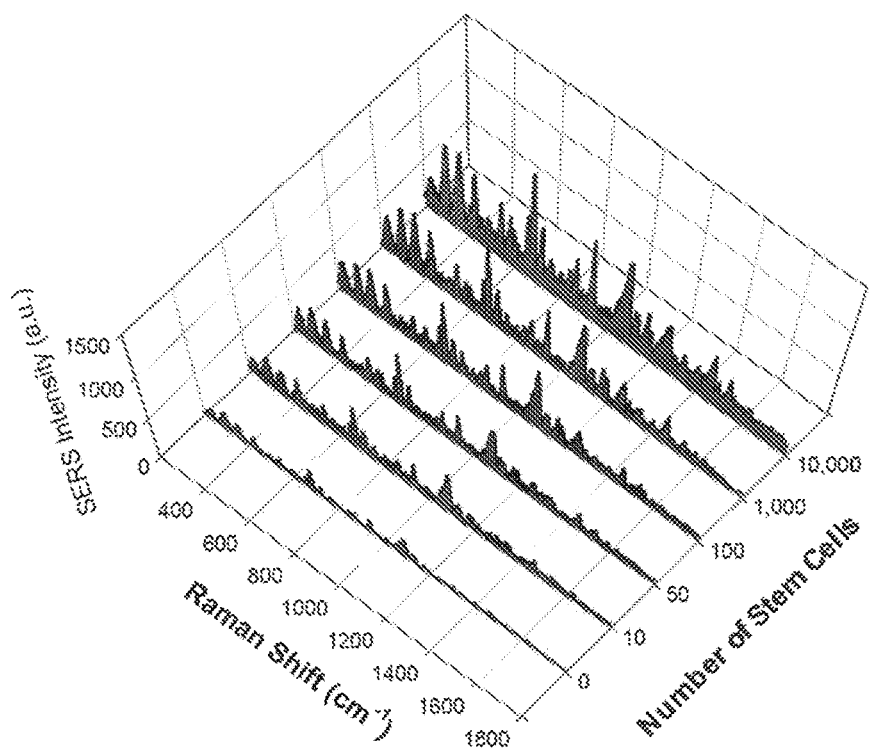
FIG. 6B shows SERS spectra obtained in the multiplexing assay for detecting SSEA-5+ and TRA-1-60+ cells in cell preparations containing various amounts of stem cells.
Figure 6C:
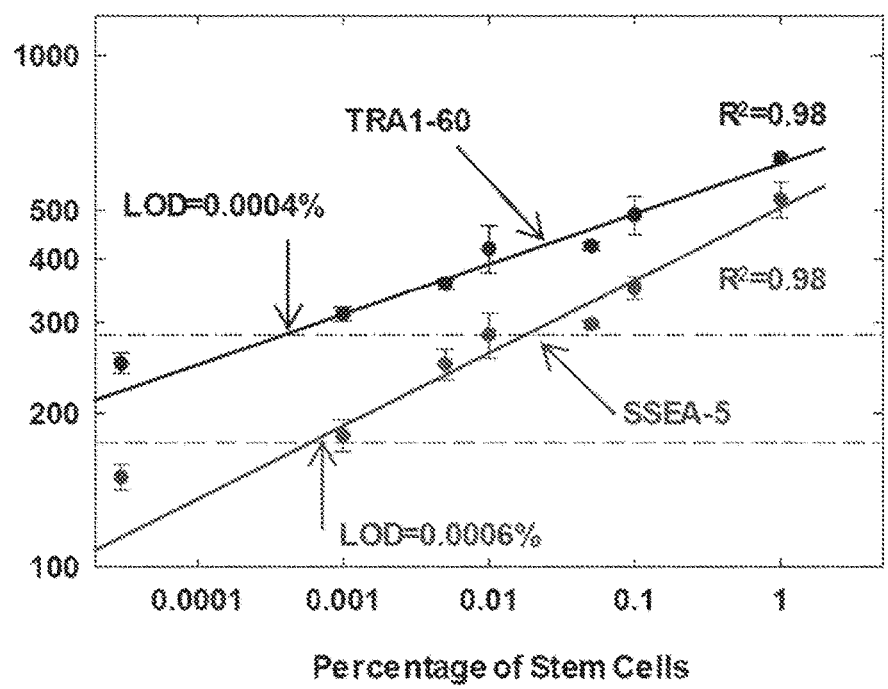
FIG. 6C shows data on the sensitivity of the SERS multiplexing assay. The LOD was determined by mean signal detected in NIH3T3 cells plus three times of the standard deviation of measurements of NIH3T3 cells.

The specificity and sensitivity of these SSEA-5- and TRA1-60-SERS nanoparticles was assessed in a multiplexing assay. Similar to the SERS assays for single surface markers, the multiplexing assay detected strong SSEA-5 and TRA1-60 SERS signals in IMR-90 iPSCs and H7 hESCs, but only negligible SERS signals in cardiomyocytes and fibroblasts (FIG. 6B), suggesting specific bindings of SSEA-5- and TRA1-60-SERS nanoparticles to stem cells. When these nanoparticles were used to detect SSEA-5+ and TRA1-60+ cells in mixed cell preparations containing various amounts of stem cells, the SERS signal intensity detected by both SSEA-5- and TRA1-60-SERS nanoparticles was positively correlated with the amount of stem cells (R2=0.98) with LOD estimated at 0.0006% for SSEA-5+ cells and 0.0004% for TRA1-60+ cells (FIG. 6C).

Figure 7A:
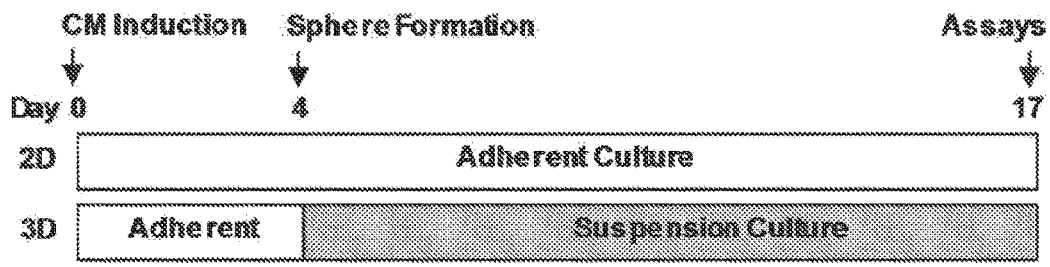
FIG. 7A illustrates and experimental design used to produce cardiomyocytes where differentiation was induced by the treatment of activin A and BMP4. At differentiation day 4, cells were dissociated and forced to form 3D spheres using a microscale technology. After 24 h, the spheres were transferred and maintained in suspension culture. At differentiation day 17, both 3D cells and the parallel 2D cultures were harvested and analyzed for cardiomyocyte purity and levels of residual SSEA-5+ and TRA1-60+ cells.
Figure 7B:
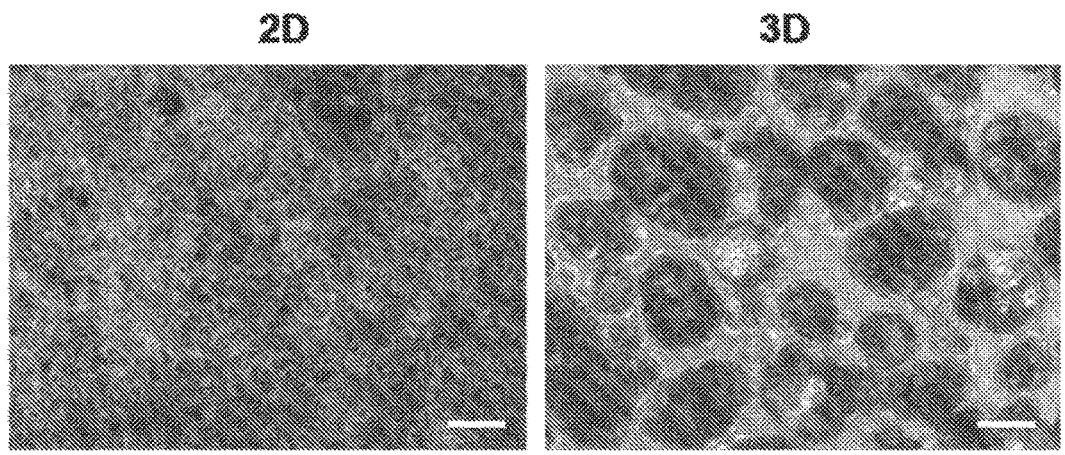
FIG. 7B shows a picture or cell morphology of 2D and 3D cultures. Scale bar=100 μm.
Figure 7C:
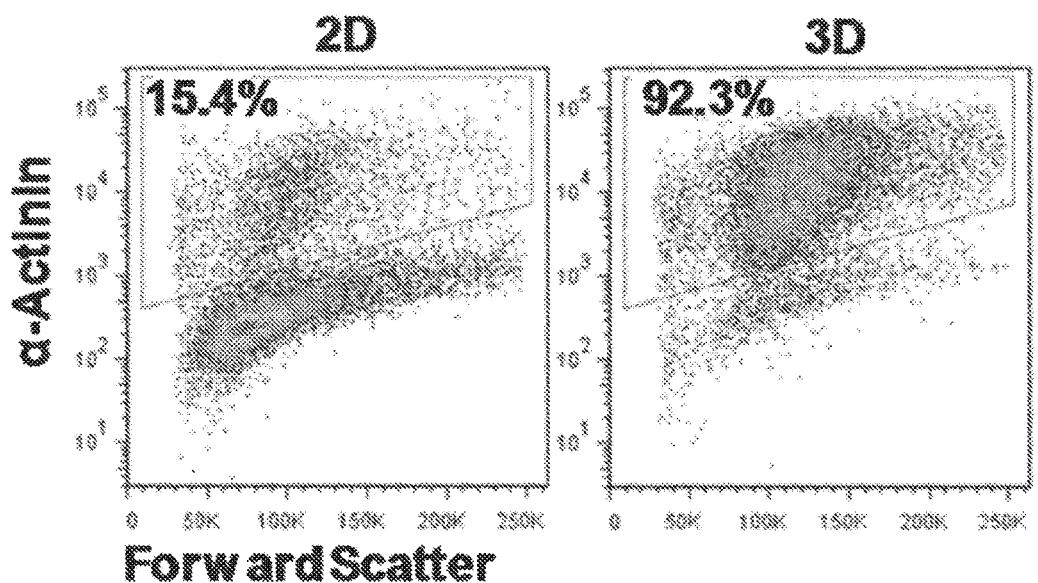
FIG. 7C shows representative flow cytometry analysis of α-actinin, a cardiomyocyte-associated marker.
Figure 7D:
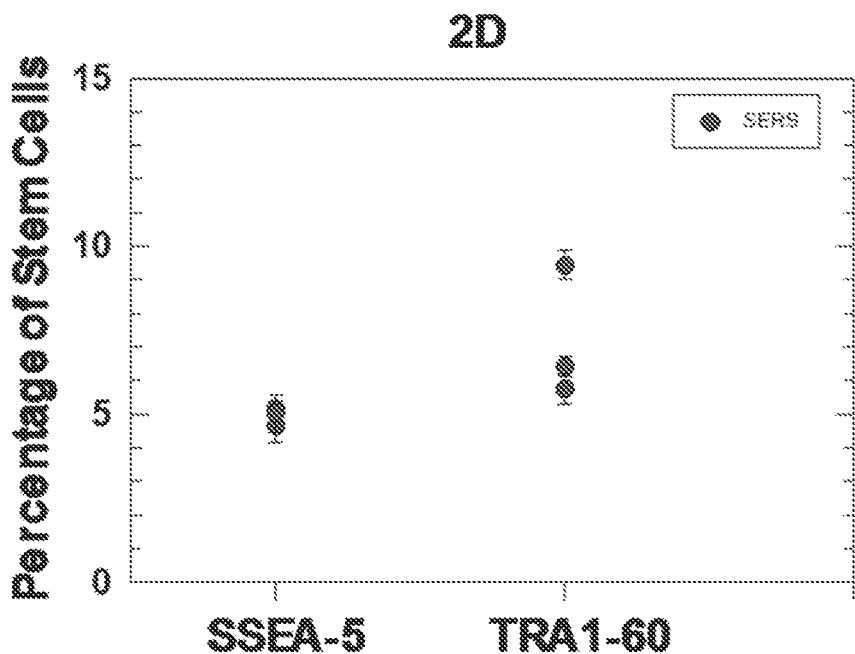
FIG. 7D shows detected levels of residual SSEA-5+ and TRA1-60+ cells in 2D cardiomyocyte differentiation cultures determined by the multiplexing SERS assay.
Figure 7E:
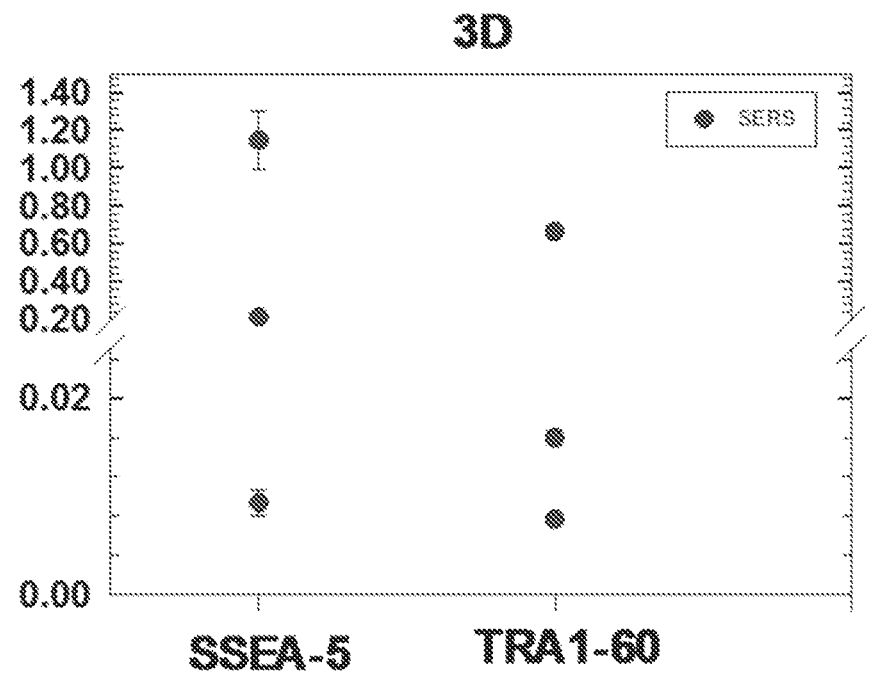
FIG. 7E shows detected levels of residual SSEA-5+ and TRA1-60+ cells in 3D cardiomyocyte differentiation cultures determined by the multiplexing SERS assay. 3D sphere cultures had reduced residual SSEA-5+ and TRA-1-60+ cells.

Detection of SSEA-5+ or TRA1-60+ Cells in Cardiomyocyte Differentiation Cultures The multiplexing SERS assays was applied to analyze residual SSEA-5+ and TRA1-60+ cells in cardiomyocyte differentiation cultures. Nguyen et al. report the microscale generation of cardiospheres promotes robust enrichment of cardiomyocytes derived from human pluripotent stem cells. Stem Cell Reports, 2014, 3:260-8. To determine whether these cardiospheres (3D spheres) contain residual SSEA-5+ and TRA1-60+ cells, cardiomyocyte differentiation from hPSCs was induced using growth factors and 3D spheres were generated at differentiation day 4 (FIG. 7A). After 24 h, the cells formed 3D spheres which were then transferred to suspension culture and maintained until differentiation day 17. The parallel 2D cultures remained as densely packed adherent cells (FIG. 7B). In both 2D and 3D cultures, beating cells were detected first at day 10 and continued to beat until harvesting. At day 17, cardiomyocyte purity was higher in 3D cultures (average of ~94%) than 2D cultures (average of ~48%) as detected by flow cytometry analysis of α-actinin, a cardiomyocyte-associated marker (FIGS. 7C and 7D). The amount of residual SSEA-5+ or TRA1-60+ cells in 2D and 3D cultures was assessed using the multiplexing SERS assay. An amount of 4.64 to 5.18% SSEA-5+ and 5.77 to 9.44% TRA1-60+ cells was detected in samples of the 2D culture, but only 0.009 to 1.15% SSEA-5+ and 0.008 to 0.665% TRA1-60+ cells were detected in samples of the 3D cultures (FIG. 7E). These results suggest that the SERS assay can be used to detect the residual SSEA-5+ and TRA1-60+ cells in cardiomyocyte differentiation cultures at very low concentrations.

The invention claimed is:

1. A method of detecting human pluripotent stem cells in a sample comprising:
    mixing a sample comprising cells suspected of containing human pluripotent stem cells with nanoparticles, wherein the nanoparticles comprise:
    a) a gold or silver core;
    b) a Raman reporter molecule next to the surface of the gold or silver core;
    c) a layer of thiol polyethylene glycol encapsulating the Raman reporter molecule; and
    d) a specific binding agent capable of selectively binding with a target cell surface marker of human pluripotent stem cells;
    wherein the mixing is done under conditions such that the specific binding agent binds target cell surface marker providing nanoparticles bound to human pluripotent stem cells;
    manipulating the sample under conditions such that nanoparticles not bound to human pluripotent stem cells are separated from the sample providing a purified sample;
    exposing the purified sample to electromagnetic radiation providing scattering associated with the Raman reporter molecule;
    detecting an intensity of scattering associated with the Raman reporter molecule being exposed to the electromagnetic radiation indicating that the human pluripotent stem cells are in the sample;
    quantifying the number of human pluripotent stem cells in the sample based on the intensity of scattering;
    and wherein the number of human pluripotent stem cells in the sample is quantified to be less than 0.01 percent of the total cells in the sample.

2. The method of claim 1, wherein the nanoparticles comprise
    a first set of nanoparticles comprising a first specific binding agent and a first Raman reporter, wherein the first specific binding agent is a SSEA-5 antibody and
    a second set of nanoparticles comprising a second specific binding agent and a second Raman reporter, wherein the second specific binding agent is a TRA1-60 antibody;
    wherein the first Raman reporter and the second Raman reporter are not the same molecule and are configured such that exposing the purified sample to electromagnetic radiation result in a first scattering intensity associated with the first Raman reporter and a second scattering intensity associated with the second Raman reporter, wherein the first scattering intensity and the second scattering intensity are at different and distinct wavelengths.

3. The method of claim 2, further comprising detecting the first and second scattering intensity.

4. The method of claim 3, further comprising quantifying the number of target cells in the sample based on the first and second scattering intensity.

5. The method of claim 1, wherein quantifying the number of target cells provides a numerical measurement, wherein the numerical measurement above a threshold value when compared to the threshold value indicates the sample is not acceptable for use in a medical application or procedure or further processing or manipulations, and wherein the numerical measurement at or below a threshold value when compared to the threshold value indicates the sample is acceptable for use in a medical application or procedure or further processing or manipulations.

6. A composition comprising a nanoparticle, wherein the nanoparticles comprise:
    a) a gold or silver core;
    b) a Raman reporter molecule about the surface of the gold or silver core;
    c) a layer of thiol polyethylene glycol encapsulating the Raman reporter molecule; and
    d) a specific binding agent capable of selectively binding with a target cell surface marker,
    wherein the specific binding agent is a pentameric TRA1-60 immunoglobulin M antibody, and
    wherein the immunoglobulin density is between 50 and 150 antibodies per particle.

7. The composition of claim 6, wherein the thiol polyethylene glycol has an average molecular weight of between 15 and 25 kDa.

8. A composition comprising a nanoparticle, wherein the nanoparticles comprise:

a) a gold or silver core;

b) a Raman reporter molecule about the surface of the gold or silver core;

c) a layer of thiol polyethylene glycol encapsulating the Raman reporter molecule; and d) a specific binding agent capable of selectively binding with a target cell surface marker, wherein the specific binding agent is a monomeric SSEA-5 immunoglobulin G antibody, and wherein the immunoglobulin density is between 15 and 30 antibodies per particle.

9. The composition of claim 8, wherein the thiol polyethylene glycol encapsulating the Raman reporter has an average molecular weight between 2 and 10 kDa.

10. The method of claim 8, wherein the binding agent is a pentameric TRA1-60 immunoglobulin M (IgM) antibody and the immunoglobulin density is between 50 and 150 antibodies per particle.

11. The method of claim 10 wherein, the thiol polyethylene glycol has an average molecular weight of between 15 and 25 kDa.

12. The method of claim 8, wherein the binding agent is a monomeric SSEA-5 immunoglobulin G antibody and the immunoglobulin density is between 15 and 30 antibodies per particle.

13. The method of claim 12, wherein the thiol polyethylene glycol encapsulating the Raman reporter has an average molecular weight between 2 and 10 kDa.

* * * * *